United States Patent
Yan et al.

(10) Patent No.: US 9,746,486 B2
(45) Date of Patent: Aug. 29, 2017

(54) SAMPLE RACK CONVEYING APPARATUS, PIPELINE AND CONVEYING METHOD USING SAME

(71) Applicant: Shenzhen Mindray Bio-Medical Electronics Co., Ltd., Shenzhen (CN)

(72) Inventors: Chang-Yin Yan, Shenzhen (CN); Li-Jian Hu, Shenzhen (CN); Jun-Hui Zheng, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 0 days.

(21) Appl. No.: 15/099,640

(22) Filed: Apr. 15, 2016

(65) Prior Publication Data

US 2016/0231343 A1   Aug. 11, 2016

Related U.S. Application Data

(63) Continuation of application No. PCT/CN2014/074246, filed on Mar. 28, 2014.

(30) Foreign Application Priority Data

Oct. 15, 2013   (CN) .......................... 2013 1 0481325

(51) Int. Cl.
*B65G 47/84* (2006.01)
*G01N 35/04* (2006.01)
(Continued)

(52) U.S. Cl.
CPC ............. *G01N 35/04* (2013.01); *B65G 37/00* (2013.01); *B65G 47/52* (2013.01);
(Continued)

(58) Field of Classification Search
CPC ...... B65G 35/06; B65G 17/002; B65G 19/02; B65G 2201/0261; B65G 47/684;
(Continued)

(56) References Cited

U.S. PATENT DOCUMENTS 3,221,781 A * 12/1965 Forsstrom ................. B01L 9/06
                                                       141/130
4,040,533 A *  8/1977 De Boer .................... B01L 9/06
                                                       198/346.2
(Continued)

FOREIGN PATENT DOCUMENTS

CN          1930479 A       3/2007
CN        101226204 A       7/2008
(Continued)

*Primary Examiner* — James R Bidwell
(74) *Attorney, Agent, or Firm* — Steven Reiss (57) ABSTRACT

The present application provides a sample rack conveying apparatus, a sample rack conveying pipeline, and a sample rack conveying method. The sample rack conveying apparatus includes a track, a detector and dual-channel track switching areas. The detector provided at an outside of the analysis areas to detect whether there is a test tube or not. The dual-channel track switching areas are defined at two ends of the track and positions between every two analysis areas. The track includes an outer track and a parallel inner track. The inner track defines at least two analysis areas. The dual-channel track switching areas include two parallel connecting channels. The connecting channels are moved along a direction perpendicular to the track to transfer the tracks between the inner track and the outer track.

23 Claims, 7 Drawing Sheets

(51) Int. Cl.
*B65G 37/00* (2006.01)
*B65G 47/52* (2006.01)

(52) U.S. Cl.
CPC ............... *G01N 2035/0412* (2013.01); *G01N 2035/0465* (2013.01); *G01N 2035/0467* (2013.01); *G01N 2035/0491* (2013.01)

(58) Field of Classification Search
CPC ............. B65G 47/52; G01N 35/04; G01N 2035/0406; G01N 2035/0412
USPC .......... 198/347.1, 465.1, 580, 465, 2, 464.2; 422/63, 65
See application file for complete search history.

(56) References Cited

U.S. PATENT DOCUMENTS

| | | | | |
|---|---|---|---|---|
| 4,454,939 | A * | 6/1984 | Kampf | G01N 35/026 198/341.02 |
| 5,232,081 | A * | 8/1993 | Kanamori | G01N 35/04 198/347.1 |
| 2004/0208787 | A1 * | 10/2004 | Takahashi | G01N 35/02 422/64 |
| 2009/0162247 | A1 * | 6/2009 | Tokieda | G01N 35/026 422/65 |
| 2010/0083772 | A1 * | 4/2010 | Tanaka | G01N 35/026 73/863.91 |
| 2015/0101911 | A1 * | 4/2015 | Friedman | G01N 35/04 198/617 |
| 2015/0233955 | A1 * | 8/2015 | Nemoto | G01N 35/04 198/602 |
| 2015/0369832 | A1 * | 12/2015 | Sacco | G01N 35/04 422/67 |
| 2016/0025756 | A1 * | 1/2016 | Pollack | G01N 35/04 436/47 |

FOREIGN PATENT DOCUMENTS

| | | |
|---|---|---|
| CN | 201965087 U | 9/2011 |
| CN | 102478583 A | 5/2012 |
| EP | 1305638 B1 | 12/2010 |
| JP | 2007309743 A | 11/2007 |

* cited by examiner

SAMPLE RACK CONVEYING APPARATUS, PIPELINE AND CONVEYING METHOD USING SAME

This application is a continuation under 35 U.S.C. §120 of international patent application No. PCT/CN2014/074246, filed on Mar. 28, 2014, which claims priority and benefit of Chinese Patent Application No. 201310481325.1, filed on Oct. 15, 2013 in the China Intellectual Property Office, the content of each application is hereby incorporated by reference.

TECHNOLOGY FIELD

The invention relates to automatic sample analysis technologies, especially relating to a sample rack conveying apparatus, a sample rack conveying pipeline, and a sample rack conveying method using same.

BACKGROUND

Laboratories performing analysis become more and more automated. Different kinds of sample analyzers, such as blood analyzers and slide pushing devices, are integrated in a sample analysis pipeline, which gives accuracy and efficiency in the analysis of a great amount of samples and is widely applied in large hospitals and institutes.

Current sample analysis pipelines usually include a loading platform to store the sample to be analyzed, an unloading platform to store the analyzed samples, and a sample rack conveying apparatus connecting the loading platform with the unloading platform. Current tracks of sample rack conveying apparatuses are usually composed of a number of track modules and a single bridge track switching mechanism connected to the track modules. Each track module includes a number of parallel tracks. Each track module corresponds to a sample analyzer. When a sample rack is transported to an analysis area on an inner track of the track module, the sample analyzer corresponding to the track module can execute an analysis of a sample container (test tube) on the sample rack.

The single bridge track switching mechanism is provided at two ends of the tracks of the sample rack conveying apparatus and between each track module. The single bridge track switching mechanism is usually a section of track movable along a direction perpendicular to the track. A length of the track is slightly longer than that of a row of the sample racks. According to a dispatch instruction, the single bridge track switching mechanism can be joined with the inner track or with the outer track of the track module, such that the sample rack is conveyed to the inner track or to the outer track. Thus, the single bridge track switching mechanism can be considered as a movable bridge between the loading platform and track modules, between every two track modules, and between the track modules and the unloading platform. As each of the tracks of the current sample rack conveying apparatuses are connected via the single bridge track switching mechanism, the outer track and the inner track of sample rack conveying apparatus cannot be connected at the same time, which leads to low efficiency.

SUMMARY

Based on those prior arts, it is necessary to supply with a more efficient sample rack conveying device, pipeline, and a conveying method using same.

A sample rack conveying apparatus disclosed herein includes a track, a detector set at an outside of the analysis areas and configured to detect whether there is a test tube or not, and a dual-channel track switching area defined at two ends of the track and at a position between every two analysis areas. The track includes an outer track and an inner track parallel to the outer track. The inner track defines at least two analysis areas. The dual-channel track switching area includes two parallel connecting channels. The connecting channels are moved along a direction perpendicular to the track to transfer the tracks between the inner track and the outer track. The connecting channels connect the inner track and the outer track at a same time.

A sample rack conveying pipeline includes a load module which includes a load area for storing a number of sample racks and a push-out channel connected to the load area. The sample rack conveying pipeline also includes an unload module which includes an unload area for storing the sample rack and a receiving channel connected to the unload area, together with the sample rack conveying apparatus mentioned above. The push-out channel is aligned with the outer track or with the inner track of one end of the sample rack conveying apparatus. The receiving channel is aligned with the outer track or with the inner track of the other end of the sample rack conveying apparatus.

A sample rack conveying method using the sample rack conveying pipeline mentioned above, includes: acquiring a start instruction of the sample rack conveying pipeline; controlling the transportation of the tracks and the track switching operation in the dual-channel track switching area and transporting the sample rack pushed out from the load module to the analysis area, wherein the dual-channel track switching area is configured to transfer the sample rack between the outer track and the inner track; controlling the detector of the analysis area to detect whether there is a specific tube or there are all the tubes on the sample rack or not; and controlling the transportation of the track and the track switching operation of dual-channel track switching area to transport the specific sample rack or all the sample racks have finished the current analysis to the next analysis area or to the unload module.

For the sample conveying apparatus mentioned above, because the dual-channel track switching area is employed, the inner track and the outer track are communicated at the same time, which improves the conveying efficiency of the sample rack. For example, when the sample rack needs to be delivered back to the upstream analyzer from the downstream analyzer, the dual-channel track switching area can make the sample rack can return more effectively.

BRIEF DESCRIPTION OF THE DRAWINGS

In the drawings, similar drawings contain similar symbols for the same device or part, or for a part which has an analogous function and/or analogous structure. It should be understood, these drawings describe different kinds of embodiments, but are not to be considered as limitations of the scope.

DETAILED DESCRIPTION

The present application is described by way of embodiments and accompanying drawings for a better understanding of present application. An exemplary embodiment of present application is illustrated in the drawings. However, the disclosure of this application can be implemented in many different ways and is not restricted by the embodiments in the present disclosure. On the contrary, the embodiments provided in this disclosure are only to indicate more comprehensive uses.

Several definitions that apply throughout this disclosure will now be presented.

When a component is defined as "fixed to" the other component, it means that the component can be directly or indirectly through intervening components fixed to the other component. When a component is defined as "connected to" the other component, it means that the component can be directly or indirectly through intervening components connected to the other component. The terms "perpendicular", "horizontal", "left", "right" and the other similar expressions used in the present disclosure are only used to explain, they are not to be considered as limiting the scope of the embodiments described herein.

The technological and scientific terms used in the present disclosure are used in accordance with normal definitions understood by those of ordinary skill in the art unless is specifically defined otherwise. The terms used in this specification are only used to describe the embodiments, not to limit the scope of the embodiments. The terms of "and/or" used in the present disclosure is defined as a group consisting of each and all the combinations of one or multiple related items.

Figure 1:
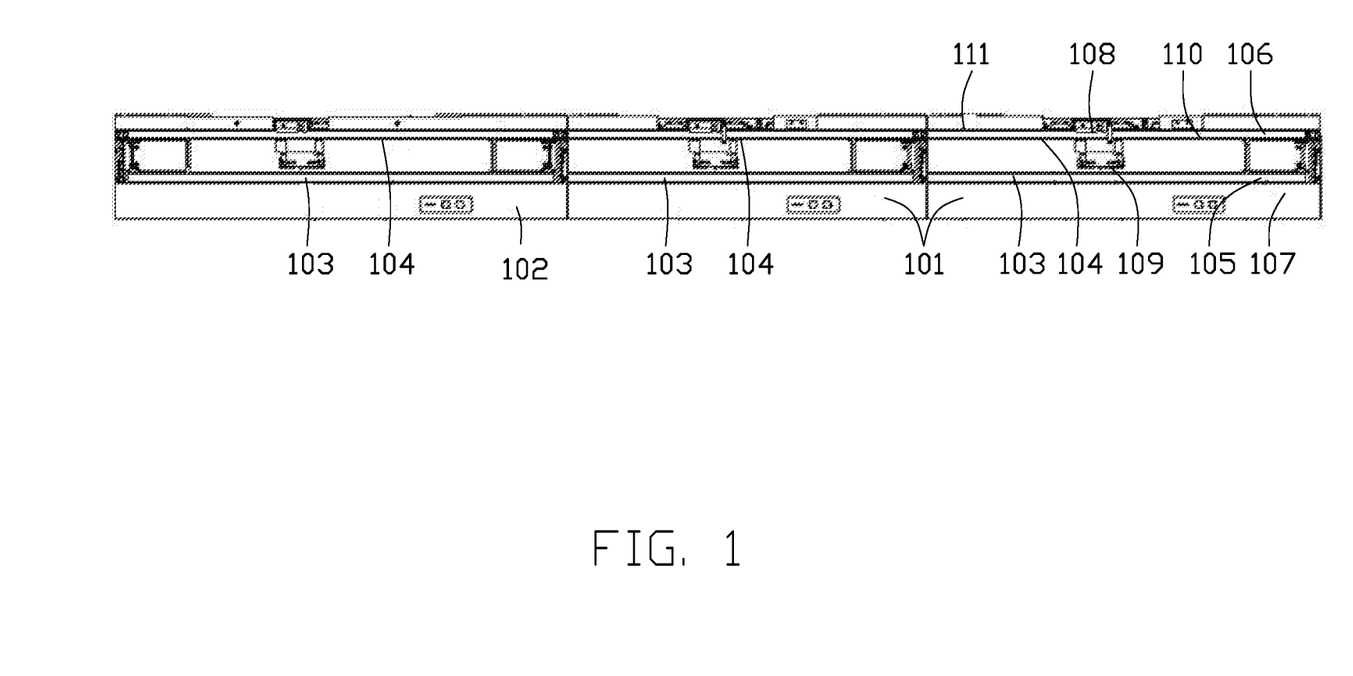
FIG. 1 is an overall schematic view of a sample rack conveying apparatus in accordance with one embodiment, the sample rack conveying apparatus includes at least one track module.
Figure 2:
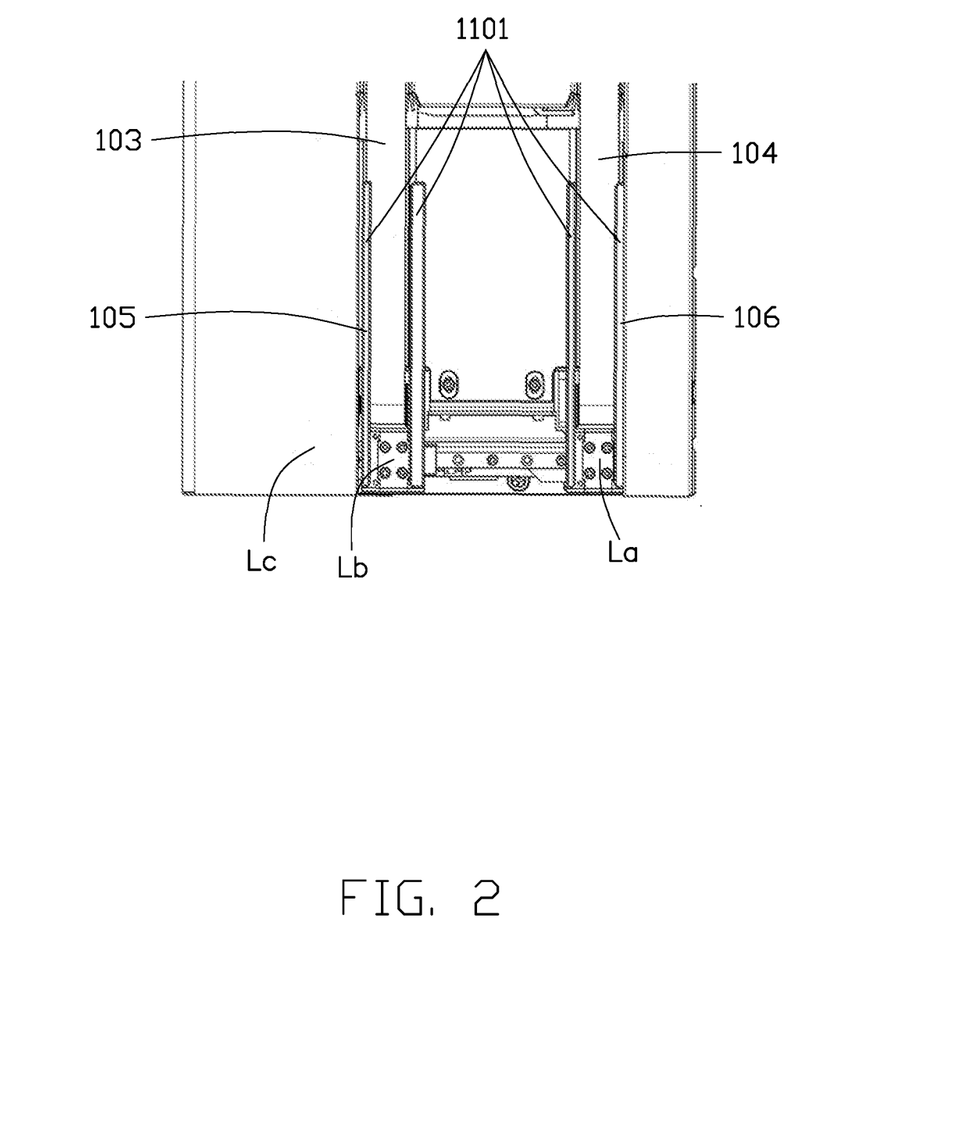
FIG. 2 is a schematic plan view of an end of the track modules of FIG. 1, the track module has a pushing structure.
Figure 3:
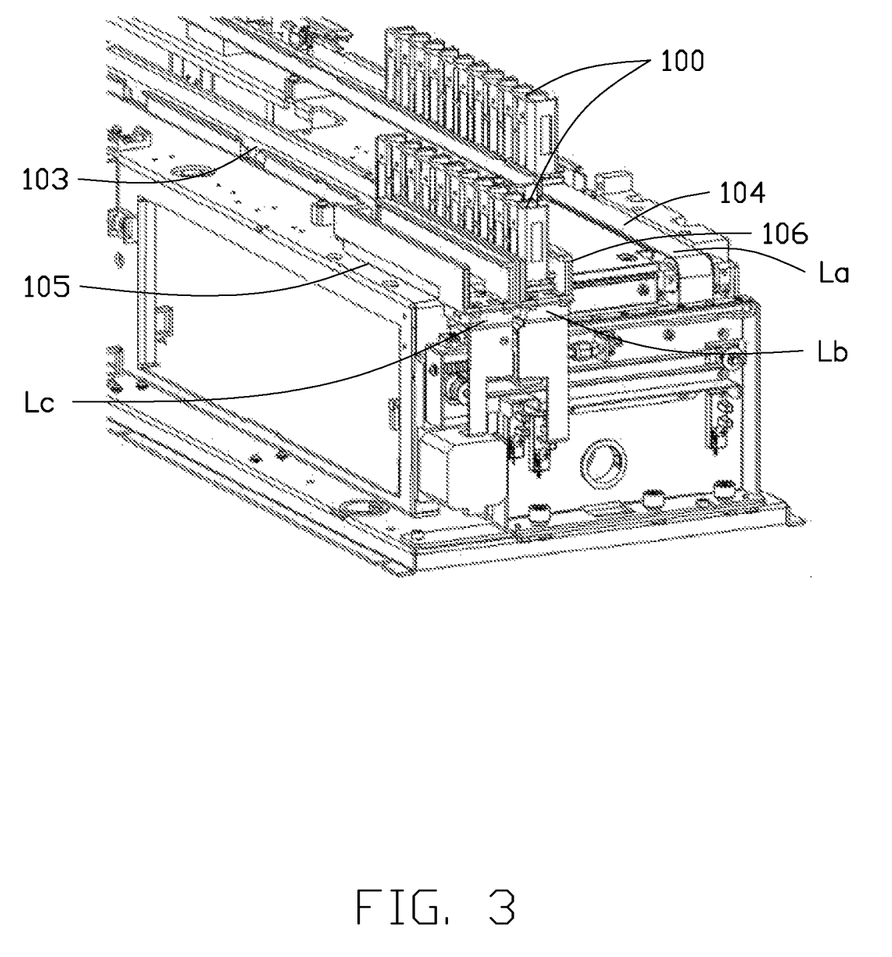
FIG. 3 is a schematic isometric view of the end of the track module in FIG. 2, with an inner switcher of the pushing structure moved to an outer track.

Referring to FIGS. 1-3, in one embodiment, a sample rack conveying apparatus includes an outer track 103 and an inner track 104 parallel to the outer track 103. In this embodiment, the track includes two first type of track modules 101 and one second type of track module 102. The ordinal of components defined in this disclosure, such as "the first" and "the second", is only used to distinguish the described component, and no priority or technological meaning is intended.

The first type of track module 101 includes the outer track 103 and the inner track 104 parallel to the outer track 103. A track switching mechanism is provided at a front end of the outer track 103 and the inner track 104. The two opposite ends of the track module are defined as a front end and a rear end. The front end is defined as the end where the sample rack is usually imported according to a conveying direction of the sample conveying pipeline. The rear end is defined as the end where the sample rack is usually exported. The denomination is only for identification, not as the technological limitation.

The track switching mechanism includes an outer switcher 105 parallel to the tracks and an inner switcher 106 parallel to the tracks. The track switching mechanism defines an outer switcher holding area 107 at an outside of the outer track 103. A numerical label is only given to each component of the track switching mechanism of one of the track modules 101 or 102 in FIG. 1. The outer switcher holding area 107 can be covered in a shell of the track module 101 and/or 102. Each of the outer switcher 105 and the inner switcher 106 includes two side walls 1101 capable of moving along a direction perpendicular to the tracks respectively. When the outer switcher 105 or the inner switcher 106 is provided on the tracks, the side wall 1101 of the outer switcher 105 or of the inner switcher 106 is defined as the track wall of the track where the outer switcher 105 or the inner switcher 106 is provided. When the inner switcher 106 is moved to the outer track 103, the outer switcher 105 which was provided on the outer track 103 is moved to the outer switcher holding area 107. That is, the track module 101 or 102 does not have a fixed track wall at the end where the track switching mechanism is provided. The movable outer switcher 105 or the inner switcher 106 is used as the track wall of the tracks. The area where the track switching mechanism located is defined as a dual-channel track switching area. The outer track 103 and the inner track 104 in the dual-channel track switching area are substantially coplanar with each other to form a track transfer area to convey the sample rack. When the sample rack is conveyed to the outer switcher 105 or to the inner switcher 106, the outer switcher 105 or the inner switcher 106 can be moved along the direction perpendicular to the track to convey the sample rack from the outer track 103 to the inner track 104, or from the inner track 104 to the outer track 103. One of the outer switcher 105 and the inner switcher 106 can be driven by a driver to actively move between the outer track 103 and the inner track 104, thus the other one of the outer switcher 105 and the inner switcher 106 is passively driven. For example, if the inner switcher 106 is actively moved to the outer track 103, the outer switcher 105 is pushed outwards to the outer switcher holding area 107. Alternatively, either one of the outer switcher 105 or the inner switcher 106 or both can be driven by the drivers. Preferably, the outer switcher 105 or the inner switcher 106 employs a single driver fashion for space saving.

Referring to FIG. 2, when the outer switcher 105 and the inner switcher 106 are respectively located on the outer track 103 and the inner track 104, that is the inner switcher 106 is located at position La and the outer switcher 105 is located at position Lb, the inner track 104 and the outer track 103 can receive the sample rack at the same time.

When the sample rack needs to be transferred from the inner track 104 to the outer track 103, the sample rack is delivered to the inner switcher 106 at first, and then the inner switcher 106 is moved to the position Lb on the outer track 103 along the direction perpendicular to the tracks. At the same time, the outer switcher 105 is moved to the outer switcher holding area 107 at the position Lc. The inner switcher 106 is returned to position La when the inner track 104 and the outer switcher 105 is returned to the position Lb on the outer track 103 after the sample rack is moved out of the inner switcher 106 to the outer track 103.

When the sample rack needs to be transferred from the outer track 103 to the inner track 104, the inner switcher 106 is moved to the outer track 103 at first and the outer switcher 105 is moved to the outer switcher holding area 107 at the same time. The sample rack is delivered in the inner switcher 106 from the outer track 103, and then the inner switcher 106 is transferred to the inner track 104 along the direction perpendicular to the tracks, the outer switcher 105 being returned to the outer track 103 from the outer switcher holding area 107.

In other embodiments, the outer switcher 105 can be set to move as the inner switcher 106. That is, an inner switcher holding area is defined at an outside of the inner track 104, and the inner switcher 106 located on the inner track 104 can be moved to the inner switcher holding area when the outer switcher 105 is transferred to the inner track 104. Thus, for flexibility of operation, the outer switcher 105 can be used to push the sample rack to the inner track 104 directly when the sample rack needs to be transferred to the inner track 104 from the outer track 103.

The second type of track module 102 also includes the outer track 103, the inner track 104 parallel to the outer track 103, and the track switching mechanism set on the front end and the rear end of the outer track 103 and the inner track 104. The detail structure of the outer track 103, the inner track 104, and of the track switching mechanism of the second type of track module 102 is similar to that of the first type of track module 101 and is not repeated.

The inner track 104 of each track module 101 and 102 includes an analysis area 108. That is, the whole inner track 104 in this embodiment includes three analysis areas 108. A detector 109 is provided outside the analysis areas 108 to detect the presence of a test tube.

In this embodiment, there are three track modules 101 and 102 sequentially connected to form the tracks of the sample rack conveying apparatus. In detail, the rear end of a first one of the first type of track module 101 is connected to the front end of a second one of the first type of track module 101. The rear end of the second one of the first type of track module 101 is connected to the front end of a first one of the second type of track module 102. The tracks are aligned to each other to enable continuous conveyance of the sample rack between different track modules 101 and 102. The outer tracks 103 of different track modules 101 and 102 are connected to each other and the inner tracks 104 of different track modules 101 and 102 are connected to each other when the different track modules 101 and 102 are connected therebetween.

There are different embodiments of the sample rack conveying apparatus. Provided that all the track modules 101 and 102 are sequentially connected to permit the disposition of the track switching mechanisms at the connection place between two analysis areas and two ends of the tracks. The inner switcher 106 and the outer switcher 105 of the pushing track mechanism can be regarded as two parallel connecting channels configured to connect the outer track 103 with the inner track 104, or to enable transfer between the inner track 104 and the outer track 103 to define the dual-channel track switching areas at two ends of the tracks and the connection place between two analysis areas.

One or more track modules 101 and 102 which have one analysis area can be considered as one unit. For example, in this embodiment, each track module 101 or 102 can be one unit. Thus, the different embodiments of the sample conveying apparatus include, but are not limited to, a first embodiment which can increase or decrease the number of the first type of track modules 101, a second embodiment which sets the track switching mechanism at the rear end of the first type of track module 101, a third embodiment in which all the track modules are made of the second type of track module 102, and a fourth embodiment which uses the second type of track module 102 to alternately connect with other track modules with no track switching mechanism at both ends.

In other embodiments, the unit can includes more than two track modules 101 and/or track module 102. The analysis area can be provided at any track module 101 and/or track module 102. The inner tracks 104 of at least two track modules 101 and/or track module 102 include the analysis area. If there is only one analysis area, the sample conveying pipeline becomes a single analyzer. In this situation, the above track modules 101 and 102 are separated into two or three sections. Thus, the track switching mechanism can set by unit at the front end and/or the rear end of the unit. The track switching mechanism can be omitted at the connection place of the track modules 101 and/or track module 102 in the same unit.

To improve the efficiency of test tube detection, the detector 109 employs an optical sensor to detect whether there is a test tube or not. The target of detection can be a test tube cap or a test tube body. In other embodiments, a physical contact sensor also can be employed as the detector 109. A non-contact sensor, like the optical sensor in this embodiment, is preferred, for example, the ultrasonic sensor, the infrared sensor, and image sensor, and so on. The reason for employing the non-contacting sensor may be reduce practice time of mechanical operation, such as an up-down mechanical movement on a test position to detect whether there is test tube located on the test position or not, to raise test speed. Therefore, the efficiency of the pipeline may be increased.

In this embodiment, in order to improve the flexibility and efficiency of the sample rack transportation, the inner track 104 of each track module 101 or 102 further includes a loading buffer area 110 and an unloading buffer area 111. The loading buffer area 110 is located in front of the analysis area 108 in the same track module 101 or 102. The unloading buffer area 111 is located behind the analysis area 108 in the same track module 101 or 102. The loading buffer area 110 and the unloading buffer area 111 are configured to receive one or more sample racks. Lengths of the loading buffer area 110 and the unloading buffer area 111 depend on the number of sample racks which need to be received. A sensor (not shown) is provided in the loading buffer area 110 to generate an "empty" signal when the loading buffer area 110 is either empty or not full. The other sensor (not shown) is provided in the unloading buffer area 111 to generate a "full" signal when a single sample rack is detected in the unloading buffer area 111 or when the unloading buffer area 111 is actually full of sample racks. The sensors can be mechanical sensors triggered by touch, or non-touch sensors such as the optical sensor or image sensor.

For the sensors in the loading buffer area 110, the loading buffer area 110 which is capable of receiving only one sample rack is determined as "empty" if a light paths of the optical sensors are not shield or turn to be exposed from being shield. The loading buffer area 110 which is capable of receiving a number of sample racks is determined as not full if the light paths of the sensors provided at a tail end of the sample rack line are not shield or turn to be exposed from being shield.

For the sensors in the unloading buffer area 111, the unloading buffer area 111 which is capable of receiving only one sample rack is determined as "full" if the light path of the sensors are blocked or turn to be unblocked from being blocked. The unloading buffer area 111 which is capable of receiving a number of sample racks is considered as there are already the sample racks in unloading buffer area 111 if the sensors provided at a front end of the sample rack line are shield or turn to be shield from being exposed. In other embodiments, where the unit consists of a number of track modules 101 and 102, the loading buffer area 110 and the unloading buffer area 111 can be set on different track modules 101 and/or 102.

In other embodiment, the loading buffer area 110 and the unloading buffer area 111 can be omitted as well. The sample rack is delivered directly to the analysis area 108 only when the analysis area 108 is free and delivered directly away from the analysis after the analysis is finished. Alternatively, one of the loading buffer area 110 and the unloading buffer area 111 can be omitted. For example, only one of the loading sample rack and the unloading sample rack is selected to be buffered. Each track module 101 or 102 of the same sample conveying apparatus can employs different kinds of buffer area configuration. For example, some track modules 101 and/or 102 include both of the loading buffer area 110 and the unloading buffer area 111. The other track modules 101 and/or 102 only include one of the loading buffer area 110 and the unloading buffer area 111 or include none of the loading buffer area 110 and the unloading buffer area 111.

In this embodiment, the loading buffer area 110 is adjacent to the analysis area 108. That is, the last test tube on the sample rack in the analysis area 108 is adjacent to the first test tube on the sample rack in the loading buffer area 110 without any gap therebetween. Thus, the analyzer can immediately deal with the next sample rack when the current analysis for the sample rack in the analysis area 110 is finished so as to improve the analysis efficiency. In other embodiments, a retractable blocker can be provided between the loading buffer area 110 and the analysis area 108 to separate the sample racks in the loading buffer area from the analysis area. The blocker blocks the sample racks in the loading buffer area 110 when there are sample racks in the analysis area 108, to separate the front end of sample racks in the loading buffer area from the tail end of the sample racks in the analysis area 108. The blocker is retracted when the analyzer is idle, and then the sample racks in the loading buffer area are delivered into the analysis area 108.

In this embodiment of the sample conveying apparatus, the track modules 101 and 102 are aligned to connect with each other, and the inner switcher 106 and the outer switcher 105 are provided on the inner track 104 and the outer track 103 to make the inner track 104 and the outer track 103 can operate at the same time. Thus, the conveying efficiency of the sample rack is improved. Furthermore, the track switching mechanism to switch the sample racks between the inner tracks 104 and the outer track 103 is a simple structure, which reduces cost.

In other embodiment, a double bridge track switching mechanism is implemented as the dual-channel track switching area. In this embodiment, the sample rack conveying apparatus includes an inner track and an outer track parallel to the inner track. The track includes two track modules and three double bridge track switching mechanisms. In other embodiment, the track includes more track modules and double bridge track switching mechanisms.

In other embodiment, a double bridge track switching mechanism is implemented as the dual-channel track switching area. In this embodiment, the sample rack conveying apparatus includes an inner track and an outer track parallel to the inner track. The track includes two track modules and three double bridge track switching mechanisms. In other embodiment, the track includes more track modules and double bridge track switching mechanisms.

Each track module includes the inner track and the outer track parallel to the inner track. The double bridge track switching mechanism includes a movable inner track and a movable outer track. The movable inner track and the movable outer track can be moved perpendicular to the track and can be connected to the inner track and the outer track of the adjacent track module. For example, the structure of a single movable outer track and inner track is similar to the structure of a current single bridge track transfer mechanism.

The inner track of each track module includes an analysis area. Thus, the whole inner track includes three analysis areas. A detector is provided at outside of each analysis area to detect the presence of a test tube.

In this embodiment, the track modules and the double bridge track switching mechanisms are sequentially connected to provide a double bridge track switching mechanism at two ends of the tracks and a double bridge track switching mechanism at positions located between each track module. The double bridge track switching mechanism defines a dual-channel track switcher. The movable outer track and the movable inner track can be regarded as two parallel connecting channels which can enable communication between the outer track and the inner track, or permit transfers between the outer track and the inner track.

The sample track conveying apparatus can include different embodiments as long as all the track modules and the double bridge track switching mechanisms are sequentially connected to set the dual-channel track switching area at two ends of the tracks and at positions located between every two analysis areas.

One or more track modules having one analysis area can be regarded as one unit. In this embodiment, each track module can be one unit. Every track module is connected to another by the double bridge track switching mechanism. The number of track modules can increase or decrease according to the number of analyzers. In other embodiments, more than two track modules can be connected to become one unit. Every unit can be connected with another unit via the double bridge track switching mechanism. The analysis area is located at one of the track modules in the unit, similar to the layout in the embodiments above, and is not repeated here.

In this embodiment, in order to improve the efficiency of tube detection, the detector employs an optical sensor. In this embodiment, the track module further includes loading buffer area and unloading buffer area as described in embodiments above, and is not repeated here.

In this embodiment of the sample conveying apparatus, the double bridge track switching mechanism is implemented as the dual-channel track switching area to have the inner track and the outer track connected at the same time, which improves the conveying efficiency of the sample rack. For example, when the sample rack needs to be delivered back to an upstream analyzer from a downstream analyzer, implementation of the dual-channel track switching area can return the sample rack more effectively.

Figure 4:
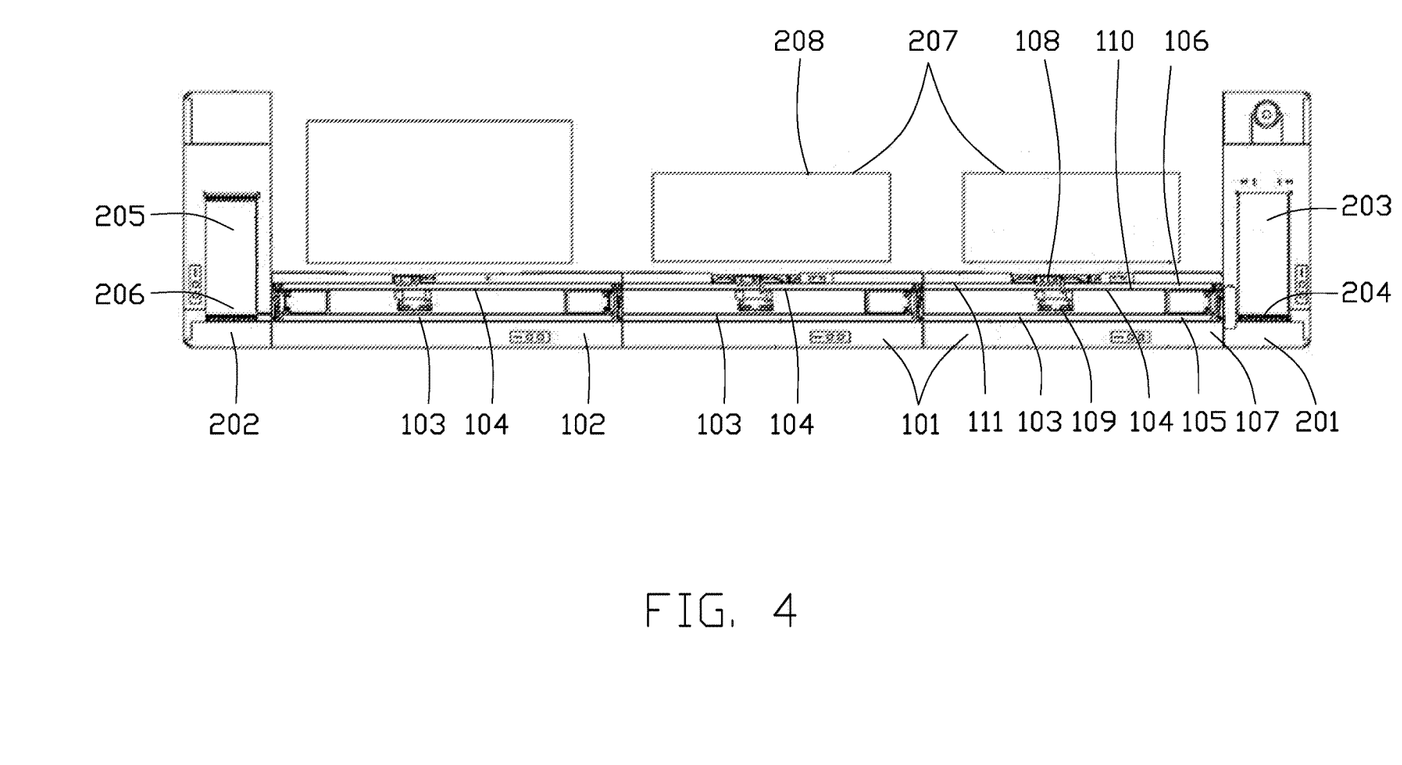
FIG. 4 is an overall schematic top view of a sample rack conveying pipeline in accordance with another exemplary embodiment.

Referring to FIG. 4, in other embodiment, the sample conveying pipeline includes a load module 201, an unload module 202, and the sample conveying apparatus. In this embodiment, the structure of the sample conveying apparatus is as implemented by the embodiments above. In other embodiments, the structure of the sample conveying apparatus can be employed by different structure transformation.

The load module 201 includes a load area 203 for storing the sample rack and a push-out channel 204 connected to the load area 203. The unload module 202 includes an unload area 205 for storing the sample rack and a receive channel 206 connected to the unload area 205.

In this embodiment, the push-out channel 204 is aligned to the outer track 103 at one end of the sample conveying apparatus. The receive channel 206 is aligned to the outer track 203 at the other end of the sample conveying apparatus. In other embodiments, the inner track 104 at two ends of the sample conveying apparatus are aligned to the load module 201 and the unload module 202. Alternatively, the inner track 104 can be used to connect one end of the sample conveying apparatus with the load area 203, and the outer track 103 can connect the other end of the sample conveying apparatus. The advantage of connecting the outer track 103 with the load module 201 is that aligning the outer track 103 to the load module 201 can improve the conveying efficiency of the sample rack when more than half of the sample racks pushed out from the load module 201 need to be transported to the outer track 103 if there are more than two analysis areas. The outer track 103 being aligned to the unload module 202 enables direct transfer of a post-analysis sample rack to the unload module 202, which reduces the number of track-switching.

When the sample rack is transported by the sample rack conveying pipeline, same or different analyzer can be configured to each analysis area. For example, in FIG. 4, the analyzers 207 are configured to the first two track modules and a slide pushing device 208 is configured to the analysis area of the last track module. In other embodiment, an analyzer 207 is transported to each of three analysis areas. Since the inner track 104 and the outer track 103 of the sample conveying pipeline are connected at the same time, the conveying efficiency of the sample rack and the analysis efficiency of the analyzers are improved.

Figure 5:
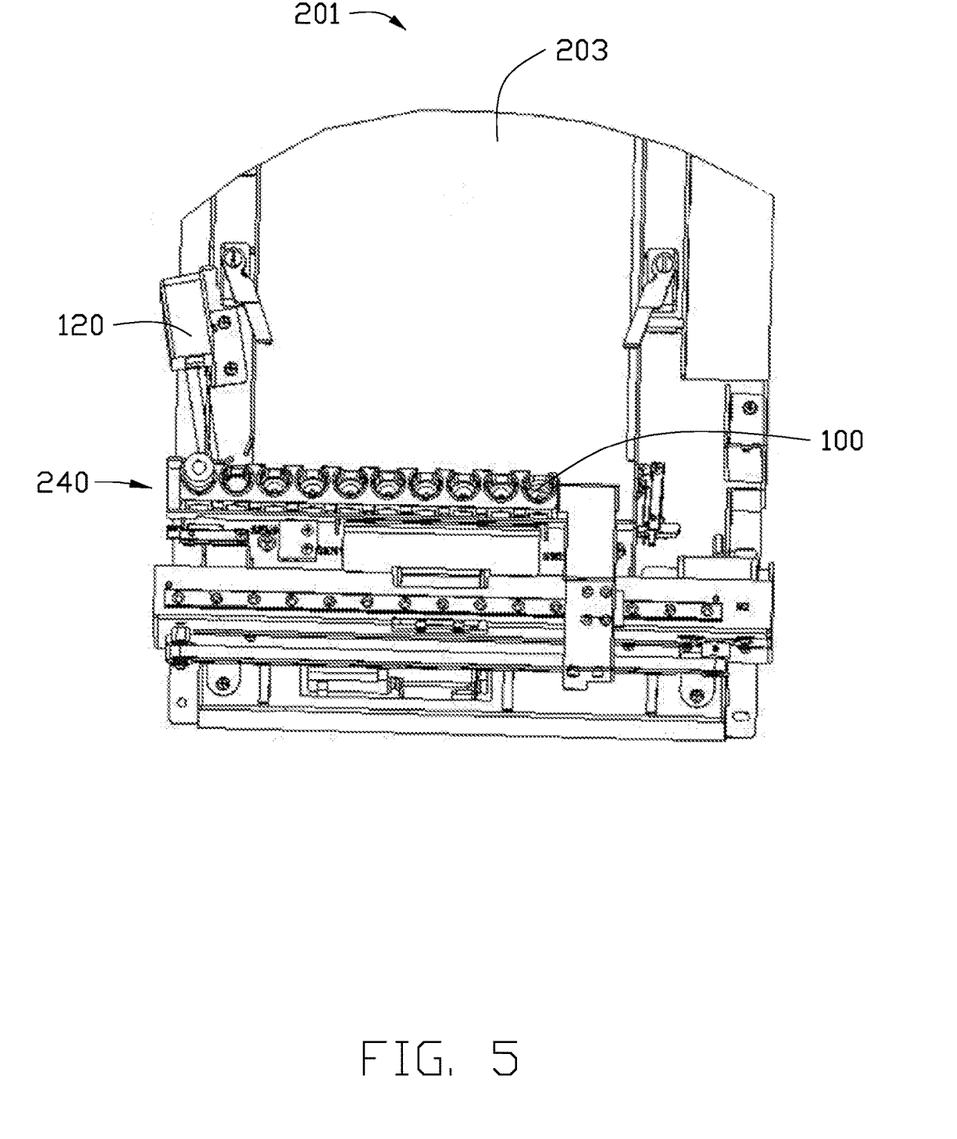
FIG. 5 is a schematic view of a loading module and scanner in the sample rack pipeline in accordance with one embodiment.

In other embodiment, the sample rack conveying pipeline also includes a scanner 120. Referring to FIG. 5, the scanner 120 is provided at an intersection point or connection of the push-out channel 204 and an end of the sample conveying apparatus. The scanner 120 scans identification tags, such as bar codes or two-dimension codes, of the sample rack 100.

In this embodiment, the scanner 120 is provided before dual-channel track switching area. That is, the sample rack is scanned before the rack enters the dual-channel track switching area. If the sample rack is found to have been delivered on the outer track 103, then a track transfer of the sample rack is not needed, and the transport efficiency of the sample rack is effectively improved.

Figure 6:
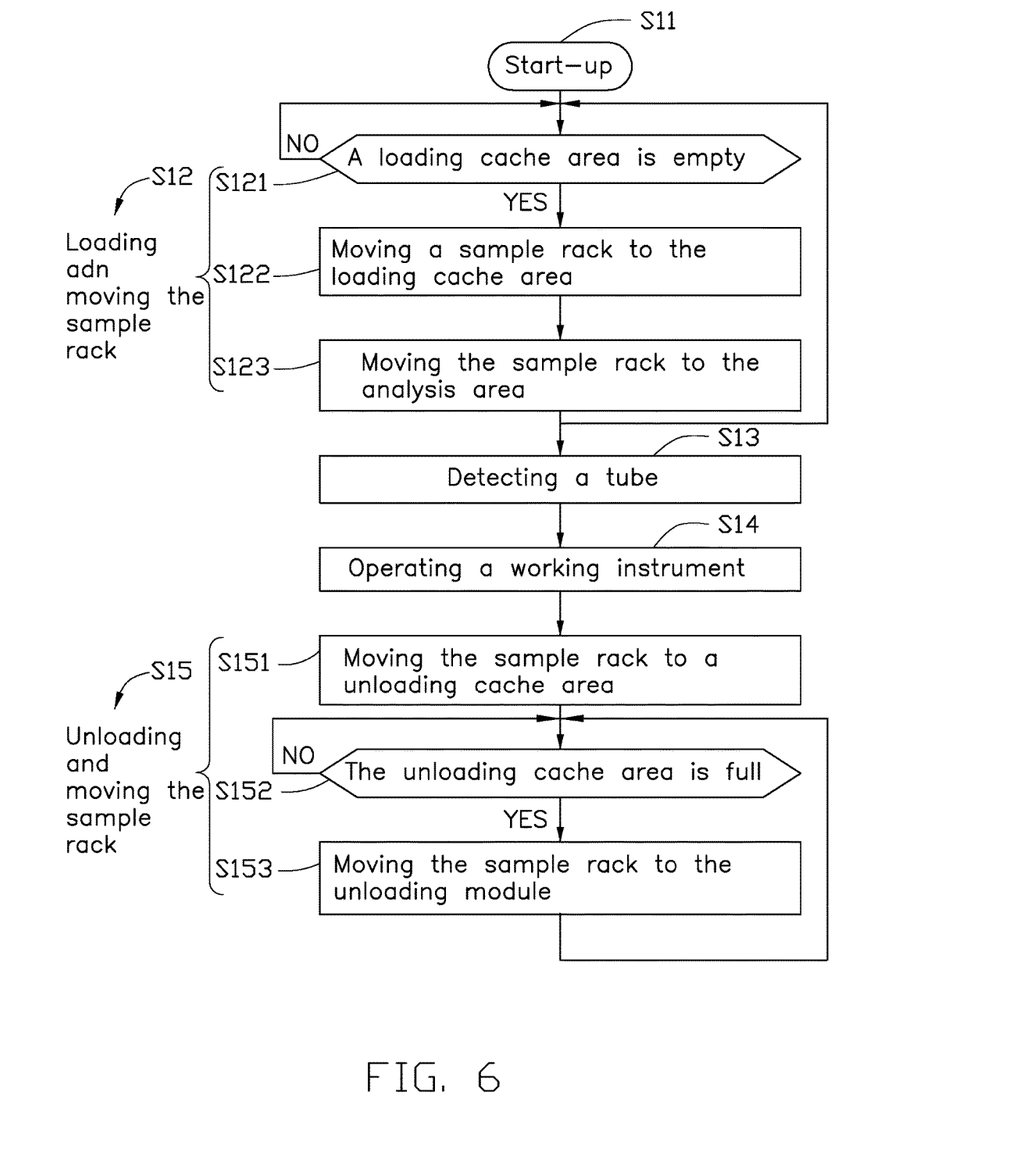
FIG. 6 is a schematic flow chart of a sample rack conveying method in accordance with one embodiment.
Figure 7:
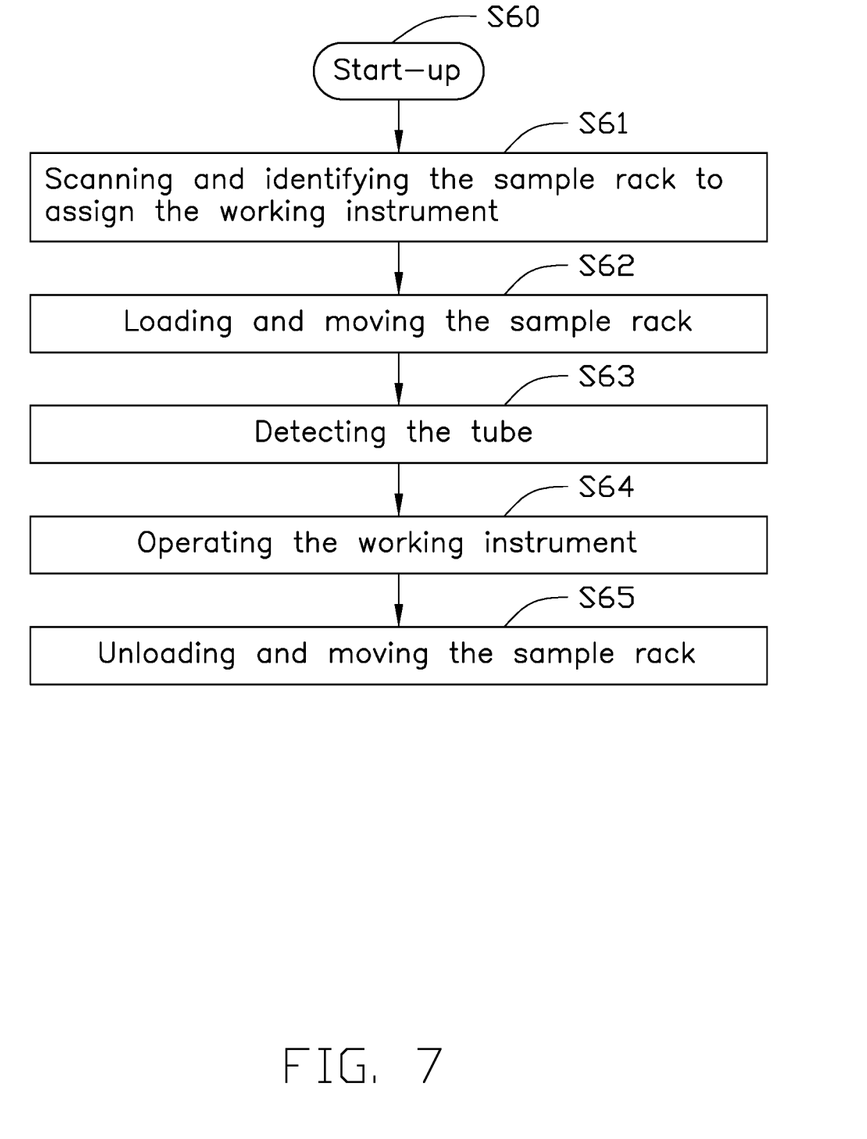
FIG. 7 is a schematic flow chart of a sample rack conveying method in accordance with the other embodiment.

Referring to FIG. 6, a flowchart is described in accordance with an embodiment of a sample rack conveying method of the sample rack conveying pipeline. The sample rack conveying method is provided by way of example, as there are a variety of ways to carry out the method. Each block shown in FIGS. 6 and 7 represents one or more processes, methods, or blocks, and the order set out is exemplary only, the order of the blocks can change. The embodiment of the component analysis method can begin at block S11.

At block S11, start conveying the sample rack, to acquire a start instruction of the sample rack conveying pipeline. The start instruction can be generated according to software operation or hardware operation. The start instruction also can be automatic generated by the load module 201 when the sample racks loaded into the load area 203 is detected by the detector 109.

At block S12, loading assignment, to control the transportation of the tracks and the track switching operation in the dual-channel track switching area. The sample racks pushed out from the load module 201 are transported to the analysis area 108 where the appropriate analyzers are located. During this process, the dual-channel track switching area is used to transfer the sample rack between the outer track 103 and the inner track 104. The detailed track switching method is mentioned above and is not repeatedly described here.

If the track modules define the loading buffer area 110 on the inner track 104, the sample rack is transported to the loading buffer area 110 at first before being transported to the analysis area. The embodiment of the load assignment about the loading buffer area 110 can begin at block S121.

At block S121, determining the status of the loading buffer area, to determine whether the detector 109 in the loading buffer area 110 generates the "empty" signal or not. If the detector 109 fails to generate the "empty" signal, the detection is carried on until the "empty" signal is detected.

At block S122, transporting the sample rack to the loading buffer area 110, the sample racks are transported to the loading buffer area 110 from the load module 201 or the analysis area of the last used analyzer. It is noted that the transported sample rack can be the untreated sample racks from the load module 201 and also can be the sample racks have been analyzed in the other analysis area. For example, the user is able to configure the position of the sample rack via the interface of a software to transport the sample rack to a specific analyzer. The user is also able to configure a number of transporting conditions via the interface of the software to transport the sample rack to the next analyzer when the analysis result satisfy or do not satisfy the predetermined transporting conditions.

At block S123, transporting the sample rack to the analysis area, the sample rack in the loading buffer area 110 is transported to the analysis area. The block S121 to block S123 can be repeatedly executed. If the analysis area is connected with the loading buffer area 110, the sample racks in the loading buffer area 110 are delivered into the analysis area following with the sample racks delivered out of the analysis area. If the loading buffer area 110 be separated from the analysis area by the retractable blocker, the blocker is retracted back to let the sample racks in the loading buffer area 110 is delivered into the analysis area when the sample racks in the analysis area are moved out. It is noted that, if the loading buffer area 110 can be omitted, the sample racks are directly transported to the analysis area. This assignment is suitable to the analysis for the single specific sample rack.

At block S13, detecting whether the test tubes exist, the detector 109 is controlled to detect whether there is a specific test tube on the sample rack or all the test tubes on the sample rack or not. The user can set the test tube needs to be analyzed via the interface of the software. Thus, the detector 109 can detect whether there is a test tube on the specific test tube holder or not and also can detect all the test tube holders. The overall detection for the test tubes does not reduce the detection efficiency if the non-contacting detection is implemented.

At block S14, analyzing the sample, the analyzer is executed the operation to the specific test tube has been detected as "YES" condition or all the test tubes have been detected as "YES" condition. The analyzers can execute operations to the test tubes in the analysis area according to the setting of the user. For example, in a pipeline mode, the analyzers sequentially execute operation to all the detected test tubes. In a specific mode, the analyzers only execute operations to the specific test tube and do not execute operation to the other test tubes. The operations can be a sample analysis or a slide staining process.

At block S15, unload assignment, to control the transportation of the tracks and the track switching operation in the dual-channel track switching area in order to transport the sample racks to the next analysis area where the appropriate analyzer are located. For example, the sample rack can be transported to the downstream analyzer, back to the upstream analyzer, or the unload module 202. If the inner track of the track module includes the unloading buffer area 111, the sample racks are transported to the unloading buffer area 111 before being transported to the next analysis area and the unload module 202. The embodiment of the unload assignment about the unloading buffer area 110 can begin at block S151 and include three steps disclosed below.

At block 151 transporting the sample rack to the unloading buffer area 111, the sample racks of which the operations is finished are transported to the adjacent unloading buffer area 111 from the current analysis area.

At block 152, determining the status of the unloading buffer area 111, to determine whether the sensor in the unloading buffer area 111 generates the "full" signal or not. If the sensor fails to generate the "full" signal, defined as "NO," the detection is carried on until the "full" signal is detected.

At block 153, transporting the sample rack to the unload module 202, the sample rack is transported to the next analysis area or the unload module 202 when the "full" signal is detected. The block S151 to the block S153 can be repeatedly executed. It is noted that, if the track module where the next analysis area is located includes the loading buffer area 110, the block S121 to the block S123 can be executed.

In the other embodiment, if the track modules do not include loading buffer area 110 or unloading buffer area 111, the step of transporting the sample rack to the corresponding buffer area is omitted. For example, if the track modules do not include the loading buffer area 110, the sample racks is directly transported to the analysis area when the analysis area is free. If the track modules do not include the unloading buffer area 111, the sample rack is transported to the unload module 202 after the operation of sample rack is finish in the analysis area. For this sample rack conveying method, the inner track and the outer track can be connected at the same time by implementing the dual-channel track switching for transporting. Under this configuration, the conveying efficiency of sample racks is improved. Furthermore, the loading buffer area 110 can receive the sample racks for waiting transportation even when the analysis area is not free yet. The unloading buffer area 111 can receive the sample racks of which the operations are finished to avoid from blocking the operation in the analysis area and provide more flexible and better assignment of sample rack. Thus, the working efficiency of analyzers, the conveying efficiency of sample rack, and the usage rate of the free tracks are improved.

Referring to FIG. 7, a flowchart is described in accordance with the other embodiment of a sample rack conveying method of the sample rack conveying pipeline, which is similar to the embodiment mentioned above, the difference there between is that the embodiment of sample rack conveying method in accordance with FIG. 7 further includes block S61 before the sample rack is delivered into the first dual-channel track switching area of the sample rack conveying apparatus.

At block S61, scanning the sample rack and transporting the analyzer, the identification tag of each sample rack is scanned at first when the sample racks are pushed out of the load module 201, the appropriate analyzer is determined according to the identification tag, and then the sample rack is transported to the analysis area where the appropriate analyzer is located.

The rest blocks, such as block S60 start conveying the sample rack, block S62 loading assignment, block S63 detecting the test tubes, block S64 operating the analyzers, and block S65 unload assignment are similar to the embodiment of sample rack conveying method in accordance with FIG. 6 and is not repeatedly described here.

In this embodiment, because sample racks are scanned to recognize the identification before entering the dual-channel track switching area and is transported to the appropriate analyzer, the dual-channel track switching area can get ready to straight transportation or track transfer before entering of sample rack and omit the scan process after the sample racks have entered in the rack transfer area. At most situations, the sample racks can be straight transported to the appropriate analyzer without many unnecessary rack transferring operations, so that the conveying efficiency is improved.

The above-described contents are detailed with specific and preferred embodiments for the present disclosure. The implementation of the present disclosure is not to be limited to these illustrations. For one of ordinary skill in the art, variations and equivalents having the same effects and applications can be made without departing from the spirit of the present disclosure and are to be considered as belonging to the scope of the present disclosure.

What is claimed is:

1. A sample rack conveying apparatus, comprising:
   a track comprising an outer track and an inner track parallel to the outer track, wherein the inner track defines at least two analysis areas;
   a detector provided at a side of the analysis areas for detecting whether there is a test tube or not; and
   dual-channel track switching areas defined at two ends of the track and at a position between the analysis areas;
   wherein the dual-channel track switching areas comprise two parallel connecting channels, the parallel connecting channels are capable of moving along a direction perpendicular to the track between the inner track and the outer track, the parallel connecting channels are capable of connecting with the inner track and the outer track at the same time;
   wherein the track comprises at least two track modules, each track module comprises a portion of the outer track, a portion of the inner track parallel to the outer track, and a track switching mechanism provided on at least one end of the track module, the track switching mechanism is located at the dual-channel track switching areas;
   the track switching mechanism comprises an inner switcher and an outer switcher both parallel to the track, and an outer switcher holding area defined at an outside of the outer track;
   each of the inner switcher and the outer switcher comprises two side walls capable of moving along the direction perpendicular to the track,
   wherein the side walls of the outer switcher and the inner switcher are configured as a track wall of part of the track when the inner switcher or the outer switcher is located on the track, and the outer switcher is moved to the outer switcher holding area when the inner switcher is switched to the outer track;
   the inner track of the track modules comprises the analysis areas, and all of the track modules are sequentially connected to provide the dual-channel track switching areas at two ends of the track and an intersection between the two analysis areas respectively.

2. The sample rack conveying apparatus of claim 1, wherein the track modules comprise a first type of track module and a second type of track module, the track switching mechanisms are provided on a front end or a rear end of the first type of track module and on a front end and a rear end of the second type of track module respectively, and the inner track of each of the track modules comprises a respective one of the analysis areas.

3. The sample rack conveying apparatus of claim 1, wherein the inner track of at least one track module further comprises a loading buffer area provided in front of the analysis area of the same track module, the loading buffer area is provided to receive the sample racks and comprises a sensor, and the sensor generates a triggering signal when a state that the loading buffer area is either empty or not full is detected.

4. The sample rack conveying apparatus of claim 3, wherein the loading buffer area is connected to the analysis area of the track module, or
the loading buffer area comprises a retractable blocker provided between the loading buffer area and the analysis area to separate the sample racks in the loading buffer area from the analysis area.

5. The sample rack conveying apparatus of claim 1, wherein the inner track of at least one track module further comprises an unloading buffer area located behind the analysis area of the same track module, the unloading buffer area is provided to receive the sample racks and comprises a sensor, and the sensor generates a full signal when a state that the unloading buffer area is full is detected.

6. The sample rack conveying apparatus of claim 1, wherein the detector is implemented by a non-contacting sensor to detect if there is a test tube or not.

7. The sample rack conveying apparatus of claim 6, wherein the non-contacting sensor is selected from a group consisting of an optical sensor, an ultrasonic sensor, an infrared sensor, and an image sensor.

8. A sample rack conveying pipeline, comprising:
a load module, which comprises a load area for storing sample racks and a push-out channel connected to the load area;
an unload module, which comprises an unload area for storing the sample racks and a receiving channel connected to the unload area; and
the sample rack conveying apparatus of claim 1,
wherein the push-out channel is aligned with the outer track or the inner track at one end of the sample rack conveying apparatus, and the receiving channel is aligned with the outer track or the inner track at the other end of the sample rack conveying apparatus.

9. The sample rack conveying pipeline of claim 8, wherein the push-out channel is aligned with the outer track at one end of the sample rack conveying apparatus, and the receiving channel is aligned with the outer track at the other end of the sample rack conveying apparatus.

10. The sample rack conveying pipeline of claim 8 further comprising a scanner for scanning an identification tag of each sample rack when the sample rack is waiting for push-out, and the scanner is configured at an intersection part of the push-out channel connecting with an end of the sample conveying apparatus.

11. A sample rack conveying method of the sample rack conveying pipeline of claim 8, comprising:
acquiring a starting instruction of the sample rack conveying pipeline;
controlling a transport mechanism on the inner and outer tracks and a track switching operation in a dual-channel track switching area, and transporting the sample racks pushed out of the load module to an analysis area, wherein the dual-channel track switching area is provided to switch the sample racks between the outer track and the inner track;
controlling the detector of the analysis area to detect the presence of a test tube in a designated position of a sample rack, or the presence of a test tube in each position of the sample rack; and
controlling transportation of the sample racks and a track switching operation of another dual-channel track switching area to transport sample racks completed with analysis to another analysis area or to the unload module.

12. The sample rack conveying method of claim 11, wherein the inner track of the track module further comprises a loading buffer area, and the method further comprising:
transporting the sample racks to the loading buffer area before the sample racks are transported to the analysis area, and
transporting the sample racks to the loading buffer area from the load module or the analysis area where the analysis of the sample racks has completed when a sensor in the loading buffer area generates the "empty" signal.

13. The sample rack conveying method of claim 11, wherein the inner track of the track module comprises the unload buffer area, and the method further comprising:
transporting the sample racks to an unloading buffer area before the sample rack area transported to the next analysis area where the sample racks are going to be analyzed or the unload module, and
transporting the sample racks to the next analysis area where the sample racks are going to be analyzed or the unload module from the unloading buffer area when a sensor in the unloading buffer area generates the full signal.

14. The sample rack conveying method of claim 11, wherein the sample rack conveying pipeline further comprises a scanner, and the method further comprising:
scanning an identification tag of each sample rack when the sample racks are pushed out of the load module,
determining an appropriate analyzer according to the identification tag, and
transporting the sample racks to an analysis area corresponding to the appropriate analyzer.

15. A sample rack conveying apparatus, comprising:
a track comprising an outer track and an inner track parallel to the outer track, wherein the inner track defines at least two analysis areas;
a detector provided at a side of the analysis areas for detecting whether there is a test tube or not; and
dual-channel track switching areas defined at two ends of the track and at a position between the analysis areas;
wherein the dual-channel track switching areas comprise two parallel connecting channels, the parallel connecting channels are capable of moving along a direction perpendicular to the track between the inner track and the outer track, the parallel connecting channels are capable of connecting with the inner track and the outer track at the same time;
wherein the track comprises at least two track modules and at least three double-bridge track switching mechanisms, each track module comprises a portion of the outer track and a portion of the inner track parallel to the outer track, the double-bridge track switching mechanisms comprise a movable outer track and a movable inner track, the movable outer track and the movable inner track are moved along a direction perpendicular to the track and connected with the outer track and the inner track of an adjacent track module.

16. The sample rack conveying apparatus of claim 15, wherein the inner track of each track module comprises the analysis areas, and the double-bridge track switching mechanisms are configured between every two track modules.

17. The sample rack conveying apparatus of claim 16, wherein the inner track of at least one track module further comprises a loading buffer area provided in front of the analysis area of the same track module, the loading buffer area is provided to receive the sample racks and comprises a sensor, and the sensor generates a triggering signal when a state that the loading buffer area is either empty or not full is detected.

18. The sample rack conveying apparatus of claim 17, wherein the loading buffer area is connected to the analysis area of the track module, or
the loading buffer area comprises a retractable blocker provided between the loading buffer area and the analysis area to separate the sample racks in the loading buffer area from the analysis area.

19. The sample rack conveying apparatus of claim 16, wherein the inner track of at least one track module further comprises an unloading buffer area located behind the analysis area of the same track module, the unloading buffer area is provided to receive the sample racks and comprises a sensor, and the sensor generates a full signal when a state that the unloading buffer area is full is detected.

20. A sample rack conveying pipeline, comprising:
a load module, which comprises a load area for storing sample racks and a push-out channel connected to the load area;
an unload module, which comprises an unload area for storing the sample racks and a receiving channel connected to the unload area; and
the sample rack conveying apparatus of claim 15,
wherein the push-out channel is aligned with the outer track or the inner track at one end of the sample rack conveying apparatus, and the receiving channel is aligned with the outer track or the inner track at the other end of the sample rack conveying apparatus.

21. The sample rack conveying pipeline of claim 20, wherein the push-out channel is aligned with the outer track at one end of the sample rack conveying apparatus, and the receiving channel is aligned with the outer track at the other end of the sample rack conveying apparatus.

22. The sample rack conveying pipeline of claim 20 further comprising a scanner for scanning an identification tag of each sample rack when the sample rack is waiting for push-out, and the scanner is configured at an intersection part of the push-out channel connecting with an end of the sample conveying apparatus.

23. A sample rack conveying method of the sample rack conveying pipeline of claim 15, comprising:
acquiring a starting instruction of the sample rack conveying pipeline;
controlling a transport mechanism on the inner and outer tracks and a track switching operation in a dual-channel track switching area, and transporting the sample racks pushed out of the load module to an analysis area, wherein the dual-channel track switching area is provided to switch the sample racks between the outer track and the inner track;
controlling the detector of the analysis area to detect the presence of a test tube in a designated position of a sample rack, or the presence of a test tube in each position of the sample rack; and
controlling transportation of the sample racks and a track switching operation of another dual-channel track switching area to transport sample racks completed with analysis to another analysis area or to the unload module.

* * * * *